US010195216B1

United States Patent
Khayyat et al.

(10) Patent No.: US 10,195,216 B1
(45) Date of Patent: Feb. 5, 2019

(54) **ANTIMICROBIAL ACTIVITY AND OIL COMPOSITIONS OF *COSTUS SPECIOSUS* (KOEN)**

(71) Applicant: King Abdulaziz University, Jeddah (SA)

(72) Inventors: Suzan Abdulrahman Khayyat, Jeddah (SA); Manal Othman Alkattan, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 15/858,608

(22) Filed: Dec. 29, 2017

(51) Int. Cl.
| | |
|---|---|
| *A61K 31/58* | (2006.01) |
| *A61P 31/10* | (2006.01) |
| *A61P 31/04* | (2006.01) |
| *A61K 36/88* | (2006.01) |
| *A61K 45/06* | (2006.01) |
| *A01N 65/40* | (2009.01) |
| *A01N 43/90* | (2006.01) |
| *A61K 9/00* | (2006.01) |

(52) U.S. Cl.
CPC ............. *A61K 31/58* (2013.01); *A01N 43/90* (2013.01); *A01N 65/40* (2013.01); *A61K 9/0014* (2013.01); *A61K 36/88* (2013.01); *A61K 45/06* (2013.01); *A61P 31/04* (2018.01); *A61P 31/10* (2018.01); *A61K 2236/333* (2013.01)

(58) Field of Classification Search
None
See application file for complete search history.

(56) References Cited

FOREIGN PATENT DOCUMENTS

CN 106511204 A 3/2017

OTHER PUBLICATIONS

Rani et al (FS J Pharm Res 1:52-53, 2012) (Year: 2012).*
Jesus et al (J Anal Methods Chem 2016:1-16, published online Dec. 28, 2016) (Year: 2016).*
Pabon et al (Molecules 18:3356-3378, 2013) (Year: 2013).*
Nagwa M. Sidkey, et al., "Antimicrobial Activity of Costus Plant Extract Against Methicillin-Resistant *Staphylococcus aureus* (MRSA, $I_3$)", International Journal of Science and Research (IJSR), vol. 4, Issue 11, Nov. 2015, pp. 348-359.
V. N. Ariharan, et al., "Antibacterial activity of Costus speciosus rhizome extract on some pathogenic bacteria", International Journal of Advanced Life Sciences (IJALS), vol. 4, Aug. 2012. pp. 24-27.
Susan Khayyat, et al., "Phytochemical screening and antimicrobial activities of *Costus speciosus* and Sea Oust", Biomedical Research, vol. 28, Issue 1, 2017, pp. 389-393.
Eunsook MA, et al., "Epoxidation of Diosgenin, 25(R)-1,4,6-Spirostatrien-3-one and 25(R)-4,6-Spirostadien-3β-ol", Molecules, vol. 8, Issue 12, 2003, pp. 886-893.

* cited by examiner

*Primary Examiner* — Craig D Ricci
(74) *Attorney, Agent, or Firm* — Oblon, McClelland, Maier & Neustadt, L.L.P.

(57) ABSTRACT

*Costus speciosus* root extracts, especially those prepared using methanol or ethanol or those that have been engineered to contain diosgenin epoxides. Methods for treating skin, burn and wound infections using a *Costus* extract or epoxidated diosgenin component of *Costus*.

17 Claims, 7 Drawing Sheets

ANTIMICROBIAL ACTIVITY AND OIL COMPOSITIONS OF COSTUS SPECIOSUS (KOEN)

STATEMENT REGARDING PRIOR DISCLOSURES BY THE INVENTOR(S)

Aspects of this technology are described by Al-Rattan, et al., *Biomedical Research* 2017; 28 (2): 734-739 (incorporated by reference).

BACKGROUND

Field of the Invention

*Costus speciosus* extracts and extracts containing diosgenin epoxide. Methods for treating fungal, yeast and bacterial infections using *Costus* extracts.

Description of Related Art

The "background" description provided herein is for the purpose of generally presenting the context of the disclosure. Work of the presently named inventor(s), to the extent it is described in this background section, as well as aspects of the description which may not otherwise qualify as prior art at the time of filing, are neither expressly or impliedly admitted as prior art against the present invention.

Bacteria, yeast and fungal dermatophytes cause some of the most widespread diseases of human and animal skin, hair and nails. Dermatophytes, such as *Trichophyton, Microsporum*, and *Epidermophyton*, obtain nutrients from keratinous tissue in skin, hair and nails but are usually incapable of penetrating viable tissue in hosts who are not immunocompromised.

*Trichophyton, Microsporum*, and *Epidermophyton* represent three major groups of dermatophytes there being about forty recognized species within these genuses. These microorganisms are commonly associated with *tinea* (skin mycoses, ringworm) infections; Al Hasan M S, Fitzgerald M, Saoudian M, Krishnaswamy G. *Dermatology for the practicing allergist: Tinea pedis and its complications*. Clin Mol All 2004; 2: 7961-7965; Mukherjee P K, Isham N, Ghannoum M A. *Infectious Diseases of the Skin: Dermatophytosis/Onychomycosis*. Curr Clin Pathol Mol Diagnos Dermatol Dermatopathol 2011. These pathogens are easily transmitted between hosts, are widely prevalent, and persist in large human and animal reservoirs; Dahdah M J, Scher R K. *Dermatophytes*. Curr Fungal Infect Rep 2008; 2: 81-86.11. Falahati M, Akhlaghi L, Rastegar Lari A, Alaghehbandan R. *Epidemiology of dermatophytoses in an Area South of Tehran, Iran*. Mycopathol 2003; 156: 279-287. For example, examination of 1,254 human patients and isolation of skin, hair and nails samples identified *T. rubrum, T. mentegrophytes, M. gypseum* and *M. canis* dermatophytes which are associated with *tinea* (ringworm, skin mycoses); Falahati M, Akhlaghi L, Rastegar Lari A, Alaghehbandan R. *Epidemiology of dermatophytoses in an Area South of Tehran, Iran*. Mycopathol 2003; 156: 279-287.

*Microsporum* fungi are associated with a large number of human skin infections as shown by a study which analyzed *M. canis* from 944 patients who visited an outpatient clinic over a 17-year period (1993-2002) in Korea; Lee J W, Song C H, Lee S D, Kim W J, Jun B, Bang Y J. *Decreasing Prevalence of Microsporum canis Infection in Korea: Through Analysis of 944 Cases (1993-2009) and Review of Our Previous Data (1975-1992)*. Mycopathol 2012; 173: 235-239.

In addition to dermatophytes, *Candida* yeasts are frequently isolated from superficial skin infections as well as mucosal surfaces. *Candida* species from 250 diverse clinical sources isolated, Mohandas V, Ballal M. *Distribution of Candida Species in Different Clinical Samples and Their Virulence: Biofilm Formation, Proteinase and Phospholipase Production: A Study on Hospitalized Patients in Southern India*. J Glob Infect Dis 2011; 1: 4-8, and *Candida albicans* was the most frequently isolated species n mucosal surfaces and superficial infections of the skin; Raz-Pasteur A, Ullmann Y, Berdicevsky I. *The Pathogenesis of Candida Infections in a Human Skin Model: Scanning Electron Microscope Observations*. ISRN Dermatol 2011. However, cutaneous candidiasis is often an opportunistic infection.

Bacteria are also found in infected skin, nails and lair. These include *Pseudomonas, Staphylococcus* and *Brevibacterium*. For example, "Green nail syndrome" is a type of skin lesion caused by *P. aeruginosa* that causes greenish discoloration of the nails (chloronychia) and is closely associated with *tinea pedis* patients; Bisno A L. *Cutaneous infections: microbiologic and epidemiologic considerations*. J Am Med 1984; 76: 172-179. Also, *Staphylococcus aureus, Brevibacterium epidermidis* and *Pseudomonas* species have been isolated from macerated digital interspaces; Kates S G, Nordstrom K M, McGinley K J, Leyden J. *Microbial ecology of interdigital infections of toe web spaces*. J Am Acad Dermatol 1990; 22: 578-582; Kates S G, Nordstrom K M, McGinley K J, Leyden J. *Microbial ecology of interdigital infections of toe web spaces*. J Am Acad Dermatol 1990; 22: 578-582.

Mixed fungal, yeast, and/or bacterial infections are seen in deep wounds of diabetic patients and include infections by *Candida albicans, Candida tropicalis, Enterococcus faecalis, Staphylococcus aureus* and *Pseudomonas aeruginosa*. In many cases, these yeast, fungi or bacteria were found to be resistant to antibiotics such as itraconazole, amphotericin B, voriconazole and flucytosine; Citron D M, Goldstein E J, Vreni Merriam C, Lipsky B A, Abramson M A. *Bacteriology of Moderate-to-Severe Diabetic Foot Infections and In Vitro Activity of Antimicrobial Agents*. J Clin Microbiol 2001; 45: 2819-2828; Chellan G, Shivaprakash S S, Ramaiyar K, Varma A K, Varman N, Sukumaran M T, Vasukutty J R, Bal A, Kumar H. *Spectrum and Prevalence of Fungi Infecting Deep Tissues of Lower-Limb Wounds in Patients with Type 2 Diabetes*. J Clin Microbiol 2010; 48: 2097-2102.

In view of emergent antibiotic resistanceto conventional antibiotics, searches have been made for new antibiotics or herbal or non-traditional antimicrobial agents. Plants have been an important source of antibiotics for thousands of years. The World Health Organization (WHO) has estimated that up to 80% of people worldwide still rely mainly on traditional remedies such as herbs for their medicines. Plants are also alternatives to antibiotics and have fewer side effects compared to allopathic medicine; Kala C P, Dhyani P P, Sajwan B S. *Developing the medicinal plants sector in northern India: challenges and opportunities*. J Ethnobiol Ethnomed 2006; 2: 32-37. The Zingiberaceae family constitutes a prominent group of medicinal and aromatic plants which are characterized by the presence of volatile oils and oleoresins; Nahak G, Kantasahu R. *Free radical scavenging activity of rhizome of Costus speciosus* (KOEN) J. E. S M. Int J Ins Miami and L Sci 2011; 1: 62-67.

Kust, Qust or *costus* root is the dried rhizome of *Costus speciosus*. The rhizomes and roots of *Costus speciosus* exhibit certain bitter, astringent, purgative, anthelmintic, antioxidant, stimulating, and antitumor properties as well as being used to improve digestion; Nahak G, Kantasahu R. *Free radical scavenging activity of rhizome of Costus speciosus* (KOEN) J. E. S M. Int J Ins Pharm and L Sci 2011; 1: 62-67; Gupta R K. *Medicinal and Aromatic Plants with Colour Plates: Traditional and Commercial Uses* Agrotechniques Biodiversity Conservation (HB) 2010; CBS: 234-499; Nadkarni K M. Indian Materia Medica. Bombay Popular Prakashan, India, 2009; 385-386; Vijayalakshmi M A, Sarada N C. *Screening of Cost speciosus extracts for antioxidant activity.* Fitoterapia 2008; 79: 197-198; Deni B. *Encyclopaedia of Herbs*, The Royal Horticulture Society 2008; P: 181. For example, the juice of the Costus rhizome is used to relive from headache and for cooling; Gupta R K. *Medicinal and Aromatic Plants with Colour Plates. Traditional and Commercial Uses* Agrotechniques Biodiversity Conservation (HB) 2010; CBS: 234-499; Srivastava S. Singh P, Mishra G, K K, Khosa R L. *Costus specious (keukand): a review.* Der Pharmacia Sinica 2011; 2: 118. Extracted essential oil and diosgenin, a steroidal sapognein, from Costus plants has been previously demonstrated for its estrogenic effects and possible pharmaceutical exploitation; Elgendy E. Al-Ghamdy H. Thermal and. Photooxidation Reactions of the Steroids: β Sitosterol, Stigmasterol and Diosgenin. J Taiwan Pharm 2007; 59: 113-132.

In view of the continuing and emerging demands for safe, effective and economical methods for treating skin, nail and hair infections caused by dermatophytes, yeasts and/or bacteria, the inventors sought to investigate, identify, functionalize, formulate and characterize new and useful anti-microbial fractions or components of *Costus*.

BRIEF SUMMARY OF THE INVENTION

One aspect of the invention is a method for inhibiting the growth of a microorganism by contacting or exposing it to a *Costus speciosis* extract especially extracts containing epoxidized diosgenin. Representative microorganisms include dermatophytes, such as *Microsporum*, yeasts such as *Candida*, and gram-negative and gram-positive bacteria, such as *Pseudomonas* or *Staphylococcus*; especially microorganisms that colonize or infect the skin. Other aspects of the invention include methods for inhibiting the growth or viability of microorganisms with methanol or ethanol extracts of *Costus* or with extracts of essential oils of *Costas speciosis*, especially extracts of its roots. A parallel feature of the invention is directed to compositions containing *Costus speciosus* extracts.

BRIEF DESCRIPTION OF THE DRAWINGS

FIG. 8A: control.
FIG. 8B: 0.5%
and FIG. 8C: 1.25%.

DETAILED DESCRIPTION OF THE INVENTION

Figure 1:
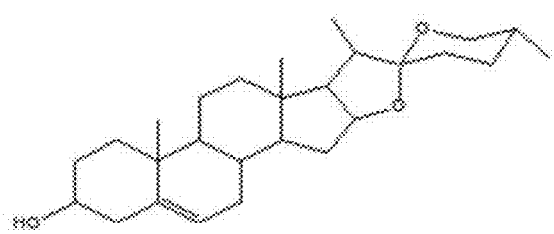
FIG. 1. Chemical structure of diosgenin.

*Costus speciosis* is also known as *Cheilo Costus speciosus*, Spiral Ginger, or Crepe Ginger. Preferably, the rhizome or roots of *Costus* are processed to make an extract. However. other components, including leaves, stems, flowers or seeds may also be extracted. These may be extracted by grinding fresh or dessicated material and then dissolving soluble components in an extraction medium such as water, methanol, ethanol, or other extractants.

Diosgenin is a phytosteroid sapogenin. It is a product of hydrolysis by acids, strong bases, or enzymes of saponins, extracted from the tubers of *Dioscorea* wild yam, such as the Kokoro. The sugar-free (aglycone) product of such hydrolysis, diosgenin is used for the commercial synthesis of cortisone, pregnenolone, progesterone, and other steroid products.

Epoxidated diosgenin derivatives according to the invention include those having the chemical structure below:

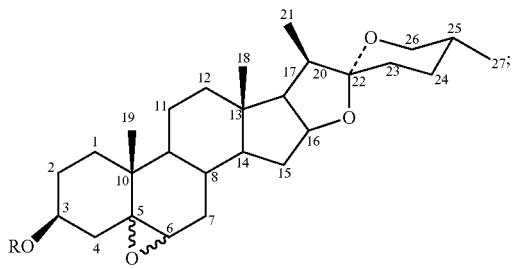

wherein R is H, C1-C6 alkyl, [hydroxy is covered by R=H]C1-C6 alkoxy, or C1-C6 carboxy; or stereoisomers thereof In preferred embodiments, R is H.

Dermatophytes include a group of three types of fungus that commonly cause skin diseases in animals and humans. These genera are: *Microsporum, Epidermophyton* and *Trichophyton*. There are about 40 species in these three genera. These include *Microsporum gypseum, Microsporum canis, Trichophyton verrucosum*, and *T. mentagrophytes*. Dermatophytes cause infections of the skins hair and nails, obtaining nutrients from keratinized material. The organisms colonize the keratin tissues causing inflammation as the host responds to metabolic by-products. Colonies of dermatophytes are usually restricted to the nonliving cornified layer of the epidermis because of their inability to penetrate viable tissue of an immunocompetent host. Invasion does elicit a host response ranging from mild to severe. Acid proteinases, elastase, keratinases, and other proteinases reportedly act as virulence factors. The development of cell-mediated immunity correlated with delayed hypersensitivity and an inflammatory response is associated with clinical cure, whereas thelack of or a defective cell-mediated immunity predisposes the host to chronic or recurrent dermatophyte infection. Some of these skin infections are known as ringworm or *tinea*. Toe nail and fingernail infections are referred to as onychomycosis. Dermatophytes usually do not invade living tissues, but colonize the outer layer of the skin. These often manifest on intertriginous areas, such as the axilla of the arm the anogenital region, skin folds of the breasts, and between digits. Occasionally the organisms do invade subcutaneous tissues. resulting in kerion development. The compositions and rrtethods disclosed herein may be used or practiced with one or more kinds of dermatophytes and the compositions and methods disclosed herein may be used to prevent or treat any of diseases, disorders or conditions associated with dermatophytes, or subjects at risk of, or infected with, a dermatophyte. Treatment with topical antifungal medicines or oral griseofulvin is common. One or more antifungal of antiyeast therapies may be used in conjugation with a composition of the invention—a (*Costus* extract or epoxidated diosgenin or diosgenin derivative. These include treatments for *tinea* as well as infection with yeasts such as *Candida*.

*Microsporum*. The genus *Microsporum* contains a number of pathogens to both humans and animals. Species include *Microsporum amazonicum, Microsporum audouinii, Microsporum boullardii, Microsporum canis, Microsporum canis* var. *distortum, Microsporum cookei, Microsporum distortum, Microsporum duboisii, Microsporum equinum, Microsporum ferrugineum, Microsporum fulvum, Microsporum gallinae, Microsporum gypseum, Microsporum langeronii, Microsporum nanum, Microsporum persicolor, Microsporum praecox, Microsporum ripariae* and *Microsporum rivalieri*. Infections involving one or more of these species may be treated according to the method of the invention.

*Microsporum canis* is a pathogenic fungus that infects the upper, dead layers of skin on domesticated cats, and occasionally dogs and humans. It is considered a zoophilic dermatophyte, given that it typically colonizes the outer surface of animal's body. *Microsporum canis* has been identified as a causal agent of a ringworm infection in pets, *tinea capitis* and *tinea corporis* in humans, and children in particular and is among the most common dermatophytes associated with *tinea capitis* and *tinea corporis*. Humans beLome infected as a result of direct or indirect contact with infected pets. *Microsporum canis* generally invades hair and skin; however, some nail infections have been reported. When hair shafts are infected, *M. canis* causes an ectothrix-type infection where the fungus envelopes the exterior of the hair shaft without the formation of internal spores, This colonization of the hair shaft causes it to become unsheathed, resulting in characteristic round or oval non-inflammatory lesions that develop on the scalp. Infection triggers an acute leukocytic reaction in subcutaneous tissues, which gradually becomes highly inflammatory and leads to hair loss, in the case of *tinea capitis. Microsporum canis* infections can be managed by topical antifungal agents; however severe cases may necessitate systemic therapy with griseofulvin, itraconazole or terbinafine. Treatment of human cases also requires the identification and elimination of the infectious reservoir, which typically involves the investigation and treatment of colonized animals and the elimination of infected bedding and other environmental reservoirs.

*Microsporum gypseum* is keratinophilic and is known for causing diseases on human skin. The diseases it causes are classified as *Tinea* or ringworm. Infection usually occurs as *Tinea capitis* (ring worm of the hair or scalp) with suppuration and kerion formation. Pus formation can also occur from palpitated hair follicles. The species can infect more than one part of the scalp at a time. The fungus produces hyphal growth at the scalp, and produces fronds or perforating organs that invade the hair perpendicularly at the cortex near the edge of the cuticles. This can cause hair to be easily removed and dislodged from the scalp. Additionally, individuals with thick dark hair have a tendency to have a more severe inflammatory response. This species is also a cause of *Tinea corporis* (ring worm of the body, especially arms and legs) and *Tinea cruris* (jock itch). *Tinea pedis* (athlete's foot) and *Tinea manum* (infection of the hand) are other infections caused by this species as is *Tinea unguium* (infection of the nails). Transmission from animals to humans may occur especially in those constrained to agricultural work. Handlers of laboratory animals. including guinea pigs, cats, and rabbits are also at risk of exposure to dermatophytes such as *Microsporum gypseum*.

Dermatophytes can infect animals that come into close contact with soil or other infected animals. Mammals such as cows, sheep, goats, oxen, and other cattle may become infected as well as horses, camels, llamas, rats, mice, guinea pigs and other rodents, rabbits, monkeys, dogs and cats. While less commonly observed in non-mammals, infections such as ring worm may occur in avians, mostly in domesticated fowl, and reptiles such as snakes, lizards, chameleons, and iguanas. Entry of the fungus or contraction of one or more of these diseases is caused by deposition on human or animal skin, and contact with soil is usually the primary cause of infection. Human to human transmission is known to occur.

Dermatophyte infections. Tinea corpora (body), tinea manus (hands), tinea cruris (groin), tinea pedis (foot) and tinea facie (face) can be treated topically. A *Costus* extract or epoxidated diosgenin derivative according to the invention may be topically or locally administered or applied in combination with one or more conventional therapies for tinea. Tinea unguum (nails) usually will require oral treatment with terbinafine, itraconizole, or griseofulvin. Griseofulvin is usually not as effective as terbinafine or itraconizole. A lacquer (Penlac) can be used daily, but is ineffective unless combined with aggressive debridement of the affected nail. Tinea capitis (scalp) is sually treated orally, as, the medication must be present deep in the hair follicles to eradicate the ftmgus. Usually griseofulvin is given orally for 2 to 3 months. Clinically dosage up to twice the recommended dose might be used due to relative resistance of some strains of dermatophytes. Tinea pedis is usually treated with topical medicines, like ketoconazole or terbinafine, and pills, or with medicines that contains miconazole, clotrimazole, or tolnaftate.

The compositions and methods disclosed herein may be used or practiced with one or more *Microsporum* species and the compositions and methods disclosed herein may be used to prevent or treat any of the above-mentioned diseases, disorders or conditions, or the subjects at risk of, or infected with, *Microsporum*, or with mixed infections of *Microsporum* with other microbes such as *Candida, Pseudomonas* or *Staphylococcus*. Subjects for therapy include humans, non-human mammals and non-mammalian animals including those who are inunimosuppressed, stressed or who otherwise exhibit impaired immunity or ance to microbial colonization or infection.

*Candida. Candida tropicalis* is a species of yeast in the genus *Candida*. It is a common pathogen neutropenic hosts, in whom it may spread through the bloodstream to peripheral organs. For invasive disease, treatments include amphotericin B, echinocandins, or extended-spectrum triazole antifungals. *C. albicans*' normal habitat is the human gut flora, mucosal membranes of humans sand various other mammals including the mouth, gut, vagina, and skin and has been identified as an opportunistic pathogen along with *C. tropicalis, C. parapsilosis* and *C. glabrata* especially in immunocompromised individuals such as those infected with HIV, undergoing immunosuppressive therapy, for example after organ or tissue transplant; or in recovery from burns. *C. albicans* has also been isolated from biofilms formed on implanted medical devices or on human tissue.

Conditions caused by *Candida* include vaginal thrush, oral thrush, armpit infection, nail infection. bedsores, and diaper rash. Yeast overgrowth can be triggered by antibiotics, steroids, menstruation, sperm, contraceptives, pregnancy, catheters, IV drips, and diabetes, Other species of *Candida* associated with candidiasis include *Candida parapsilosis* and *Candida vini* which may also be treated with a composition method as disclosed herein.

Candidiasis is usually treated with a conventional antifungal medicine. The treatment for mild to moderate infections in the mouth or throat is usually an antifungal medicine applied to the inside of the mouth for 7 to 14 days. These medications include clotrimazole, miconazole, or nystatin. For severe infixtions, the treatment is usually fluconazole or another type of antifungal medicine given by mouth or throw vein for people who don't get better after taking fluconazole. The treatment for candidiasis in the esophagus, is usually fluconazole. Other types of prescription antifungal medicines can also be used for people who can't take fluconazole or who don't get better after taking fluconazole. Doctors treat thrush with topical, antifungal medications such as nystatin (Mycostatin and others) and clotrimazole. For mild cases, a liquid version of nystatin can be swished in the mouth and swallowed, or a clotrimazole lozenge can be dissolved in the mouth. For more severe cases, fluconazole (Diflucan) can be taken once a day by mouth. *Candida* esophagitis is treated with an oral anti-fungal drug such as fluconazole. Cutaneous candidiasis can be effectively treated with a variety of antifungal powders and creams. The affected area must be kept clean and dry and protected from chafing. Vaginal yeast infections can be treated with antifungal medications that are applied directly into the vagina as tablets, creams, ointments or suppositories. These include butoconazole (Femstat), clotrimazole (Gyne-Lotrimin), miconazole (Monistat, Vagistat and others), nystatin (Mycostatin and others), and tioconazole (Monistat-1, Vagistat-1). A single dose of oral fluconazole can be used. The compositions and methods disclosed herein may be used or practiced with one or more *Candida* species alone or in combination with conventional therapies described above.

In some embodiments, besides one or more agents of the invention, as well as an antiftmgal or anti-yeast agent may be applied. These include an antifungal agent, such as a polyene antifungal, such as natamycin, rimocidin, filipin, nystatin, amphotericin B, candicin; imidazoles, such as miconazole, ketoconazole, clotrimazole, econazole, bifonazole, butoconazole, fenticonazole, isoconazole, oxiconazole, sertaconazole, sulconazole, or tioconazole; triazoles, such as fluconazole, itraconazole, isavuconazole, ravuconazole, posaconazole, voriconazole, or terconazole; thiazoles such as abafungin; allylamines, such as terbinafine, amorolfine, naftifine, or butenafine; echinocandins, such as anidulafungin, caspofungin, or micafungin; others antifungal agents such as benzoic acid, ciclopirox, tolnaftate, undecylenic acid, flucytosine or 5-fluorocytosine, griseofulvin, haloprogin, sodium bicarbonate, allicin, one or more essential oils, tea tree oil, citronella oil, iodine, lemon grass, olive leaf, orange oil, palmarosa oil, patchouli, lemon myrtle, neem seed oil, coconut oil. zinc, or selenium. In some embodiments, a *Costus* extract, *Costus* oil, epoxided *Costus* oil, disogenin, or diosgenin epoxide will contain non-toxic, undetectable or substantially no amount of aristolochic acid.

Antibacterial therapy. One or more antibacterial therapies may be used in combination with an agent of the invention, such as a *Costus* extract or epoxidated diosgenin or diosgenin derivative. Antibiotics against many strains of *Pseudomonas aeruginosa* include aminoglycosides (gentamicin, amikacin, tobramycin); quinolones (ciprofloxacin, levofloxacin); cephalosporins (ceftazidime, cefepime, cefoperazone, cefpirome, ceftobiprole); antipseudomonal penicillins: carboxypenicillins (carbenicillin and ticarcillin), and ureidopenicillins (mezlocillin, azlocillin, and piperacillin); carbapenems (meropenem, imipenem, doripenem); polymyxins (polymyxin B and colistin) and monobactams (aztreonam). Many strains of *Staphylococcus aureus* have developed antibiotic resistance. Strains that are penicillinase-resistant may be treated with penicillinase-resistant β-lactam antibiotics, such as methicillin, nafcillin, oxacillin, cloxacillin, dicloxacillin, and flucloxacillin. Other antibiotics are used to treat strains that have developed methicillin-resistance (MRSA). First-line treatment for serious invasive infections due to MRSA is glycopeptide antibiotics (vancomycin and teicoplanin). Methicillin-resistant strains may also be treated with clindamycin (a lincosamine) and co-trimoxazole (also commonly known as trimethoprim/sulfamethoxazole) or with broad-spectrum anti-gram-positive antibiotics, such as linezolid. The method of the invention may be used in place of or in combination with administration of one or more of the drugs or treatments described above.

Additive or synergistic combinations of conventional anti-*Pseudomonas* or anti-*Staphylococcus aureus* medications and an agent according to the invention (e.g., a *Costus* extract or epoxidated diosgenin) may be used to treat disease, disorders or conditions associated with *Pseudomonas* or risk of infection with *Pseudomonas*. A *Costus* extract may be included when there is a risk of resistance to a conventional anti-microbial agent or antibiotic. Local or topical use of compositions according to the invention, optionally in combination with conventional drugs, may prevent deep or invasive infections by these bacteria and other microbes.

Therapeutic Compositions of the Invention. The compositions useful herein contain a *Costus* extract or epoxidated diosgenin or a derivative thereof and may be formulated to allow for administration to a subject by any chosen route, including but not limited to topical, oral or nasal (including by inhalation), vaginal, rectal or parenteral (including topical, subcutaneous, intramuscular and intravenous) administration. Those skilled in the art will appreciate that the route of administration to a subject will typically take into account the purpose for which the composition is being administered for example, where a pharmaceutical composition of the invention is being administered to treat a disease or disorder, the route of administration will typically be chosen taking into account the nature of the disease or disorder. Accordingly, exemplary compositions for the treatment of skin, nail or hair infections or infections of mucosal membranes or deep skin wounds may be formulated for topical administration. Thus, a pharmaceutical composition useful according to the invention may be formulated with an appropriate pharmaceutically acceptable carrier (including excipients, diluents, auxiliaries, and combinations thereof) selected with regard to the intended route of administration and standard pharmaceutical practice.

The preparation of pharmaceutically acceptable carriers and formulations suitable for containing a *Costus* extract, diosgenin derivative such as epoxidated form of diosgenin is described in *Remington's Pharmaceutical Sciences*, 21st Edition, ed. University of the Sciences in Philadelphia, Lippincott. Williams & Wilkins, Philadelphia Pa., 2005, which is incorporated herein by reference in its entirety. Compositions useful herein include any composition that is able to carry or incorporate a *Costus* extract or diosgenin derivative of the invention, such as epoxidated diosgenin. Such compositions will often be formulated to be locally or topically applied because dermatophytes and other microbes described herein are usually found in the skin, hair and nails.

Non-pharmaceutical compositions containing on-sterile ingredients or ingredients not suitable for therapeutic administration such as those found in disinfectants or cleaners may also be formulated as substantially disclosed below but without a requirement for pharmacological acceptable ingredients.

pH. A composition may have an acidic or basic pH, such as a pH ranging from 1, 2, 3, 4, 5, 6, 7, 8, 9, 10, 11, 12, 13 to 14 (or any intermediate value within this range), preferably from 3 to 9, more preferably from 5.5 to 8.5. It may match or coordinate to the pH of the skin (e.g., from pH 4 to 7.0, preferably about pH 5), nails or hair, or other tissue to which it is applied or vary upward or downward by about 0.1, 0.2, 0.5, 1.0, 1.5 or 2.0 pH units from a neutral pH or from the pH of skin, hair, nails or other tissue to which it is applied. A pH may be selected to facilitate attachment to skin, hair or nails of resident microbes (e.g., normal, healthy flora, for example, from about pH 4 to 6, or to promote the dispersal of microorganisms such as dermatophytes, yeast or bacteria from skin, hair or nails, for example, at an alkaline pH such as about pH 8-9.

Compositions, including topical compositions, may be prepared as solutions, serums, lotions, creams, pastes, ointment/salves, gels, aerosols, foams and other conventional formulations using known carriers, for such applications. Such formulations may be administered directly, for example, applied directly on to a site of infection, burn, abrasion, acne, a wound. or sprayed onto a burn, wound or surgical site or may be applied indirectly, such as by impregnation into a bandage or dressing or sprayed onto surgical equipment, dressings and the like.

Ingredients used for one formulation described herein may be used in other forioulations provided that the amounts used are compatible with the physical properties and form of the particular formulation. For example, an emulsifier or antioxidant used in a lotion may also be used in a cream, gel or foam provided it does not substantially affect the fundamental nature of the cream, gel or foam.

Some ingredients will modify the physical or functional characteristics of a composition. Stabilizers, preservatives, humectants, regreasing agents, solvents or auxiliaries can be included to improve efficacy and dermal penetration. Dermal penetration-enhancing compounds provided have low toxicity to the skin and can promote percutaneous and oral mucosal absorption. In one embodiment, deiinal penetration-enhancing compounds include propylene glycol, polyethylene glycol, dimethylsulphoxide, decylmethylsulphoxide, azoles, N-methylpyrrolidone, diethyltoluarnide, ethanol, isopropyl myristate, isopropyl palmitate, oleic acid and its esters, medium-chain triglycerides, dimethyl isosorbitol, 2-octyldodecanol, branched fatty acids, benzyl alcohol, urea, salicylates and surfactants. Viscosity enhancers or thickeners can be included. Such enhancers can prevent a composition from spreading beyond the site of application.

In one embodiment, Balsam Fir is used as a viscosity enhancer. Thickeners include suitable polymers such as carbomer, hydroxypropyl methylcellulose, hydroxyethylcellulose, PVM/MA decadiene cross-polymer and acrylates. Two or more thickeners can be added.

Spreading oils or emollients can be included. One benefit for including such oils is for better distribution on surfaces, in particular on the skin. Spreading oils are understood as those oily liquids which are distributed particularly easily on the skin. They are known as such in cosmetics. The following compounds are suitable spreading agents: silicone oil, fatty acid esters, such as ethyl stearate, di-n-butyl adipate, hexyl laurate and dipropylene glycol pelargonate, esters of a branched fatty acid of medium chain length with saturated $C_{16}$-$C_{18}$ fatty alcohols, isopropyl myristate, isopropyl palmitate, caprylic/capric acid esters of saturated fatty alcohols of $C_{12}$-C18 chain length, isopropyl stearate, oleyl oleate, decyl oleate, ethyl oleate, ethyl lactate, waxy fatty acid esters, such as synthetic duck uropygial gland fat, dibutyl phthalate, diisopropyl adipate, ester mixtures related to the latter and the like. Other elements that can be included are emollients, such diisopropyl adipate/isohexadecane dimethicone, occlusive agents, such as example cyclomethicone, trimethylsiloxysilicate, glycereth-26 or polyquaternium-7, emulsifiers, such as cetyl alcohol, stearyl, stearic acid, glyceryl stearate, propylene glycol isostearoyl-sodium isostearoyl, a lactylate, polyoxyethylene (100) stearate, skin conditioners, moisturizers, humectants, such as propylene glycol or glycerin, preservatives, such as phenoxyethanol and parahens, pH adjusting agents, surfactants, chelators, such as disodium EDTA or sodium citrate, tackifying agents, fragrances and other compounds.

Solutions. A solution containing a *Costus* extract or diosgenin derivative, such as an expoxidated derivative. according to the invention will contain an extract and a liquid carrier suitable for dissolving, suspending, or emulsifying the *Costus* extract or diosgenin derivative. To standardize concentration of the extract or diosgenin derivative a dessicated or dried *Costus* extract or diosgenin derivative or material containing it may be used on a weight percentage basis. For example, a *Costus* extract prepared by extracting components solution in ethanol or methanol may be dried to remove the ethanol, methanol or other solvents and then weighed and admixed with a suitable solvent, such as a pharmaceutically acceptable carrier, at a known concentration.

Concentrations of an extract or diosgenin derivative in a solution or other therapeutic composition described herein may range from >0, 0.001, 0.002, 0.005 0.01 0.02, 0.05, 0.1, 0.2, 0.5, 1.0, 2.0, 5.0, 10.0, 20.0, 50.0 and <100 wt % of the dried extract or dry diosgenin derivative (including those derivatives described or exemplified herein). When arm extractor diosgenin derivative is already in a liquid form, it may also be applied neat. For therapeutic use a weight percentage of a solution may correspond to the minimal inhibitory dosage for a particular deimatophyte or bacterium. Minimal inhibitory dosage for a particular extract may be determined by methods known in the art including the broth dilution method or agar diffusion method, see Sela, et al., Pharmacognosy Res. 2015 Jan-Mar; 7(1): 74-80; or by Sidkey, et al., International Journal of Science and Research (IJSR) Volume 4 Issue 11, Nov. 2015 (both incorporated by reference).

A solution or other therapeutic composition may be formulated to contain a concentration of 0.1, 0.2, 0.5, 1.0, 2.0, 5.0 or 10.0 or more times the minimal inhibitory dosage for a particular dermatophyte, yeast, bacteria or other microbe, preferably, the concentration in a therapeutic composition will be 1.0 or more of the minimal inhibitory concentration, but is some applications a lower concentration may be used, for example, in a mixed composition containing other active ingredients, or for a composition that is repeatedly applied, or for subjects sensitive to particular extracts. A topical dosage of a *Costus* extract containing epoxidated diosgenin may contain 0.1, 0.2, 0.5, 1, 2, 3, 4, 5, 10, 15, 20, 25, 30, 35, 40, 45, 50 or more of the extract by weight.

Serums. A serum refers to a light, quickly absorbed composition that exposes and permits rapid uptake of an active ingredient by skin. It can be used as an alternative to heavier creams or lotions that contain occlusive, or airtight, moisturizing ingredients such as petrolatum or mineral oil that keep water from evaporating. Serums usually contain fewer lubricating and thickening agents, like nut or seed oils, than creams or lotions. Most serums are water-based or based on hydrophilic components, eliminating oils altogether. A serum may be formulated to contain a higher concentration of, an active ingredient, such as diosgenin epoxide extract, than a darn or lotion.

Lotions provided herein include liquids or semi-liquid fonnulations that are generally lower in viscosity than a cream or gel. The lotions can be an oil-in-water or water-in-oil formulation stabilized by a surface-active agent and are usually suitable for application to skin, hair or nails. They may be in a form of an emulsion and include methylcellulose, sodium carboxymethyl-cellulose, and similar compounds or contain other ingredients such as those described below for creams and other pharmaceutical compositions provided the combined amounts of the ingredients form a lotion. In one embodiment, the lotions contain suspending agents to produce better dispersions and compounds useful for localizing and holding an active agent such as a *Costus* extract or a diosgenin derivative or epoxidated diosgenin.

Creams provided herein include liquids or semi-solid emulsions with a viscous consistency. Creams can be either oil-in-water or water-in-oil based formulations. Cream bases can be water soluble. Cream bases can contain the following components: (1) an oil phase, (2) an aqueous phase, and (3) an emulsifier. he oil phase can comprise petroleum jelly and a fatty alcohol, such as cetyl or stearyl alcohol. The aqueous phase can contain a humectant. The emulsifier can be a nonionic, anionic, cationic or amphoteric surfactant. In one embodiment, the oil phase includes, but is not limited to, cetyl alcohol, stearyl alcohol, stearic acid, liquid paraffin, and dimethicone. In another embodiment, the water phase ingredient includes, but is not limited to, glycerol and ethyl paraben as well as Diosgenin epoxide aqueous extract. In another embodiment, the emulsifying agent includes, but is not limited to, fatty alcohol polyoxyethylene ether (Peregal A-20), polyoxylstearate (SG-6), or combinations thereof.

Ointments/salves provided herein include semi-solid preparations that have petroleum jelly or their derivatives as a base. Petroleum jelly is a semi-solid mixture of hydrocarbons. As described in *Remington: The Science and Practice of Pharmacy*, 19th Ed. (Easton, Pa.: Mack Publishing Co., 1995). at pages 1399-1404, ointment bases can be grouped in four classes: oleaginous bases; emulsifiable bases; emulsion bases; and water-soluble bases. Oleaginous ointment bases include vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petroleum jelly. Emulsion ointment bases are either water-in-oil or oil-in-water emulsions, and include, for example, cetyl alcohol, glyceryl monostearate, lanolin, and stearic acid. An ointment may contain solid or encapsulated particles or emulsified and suspended particles containing a *Costus* extract or diosgenin derivative or epoxide. Black Ointment, of Ichthyol Salve, also called Drawing Salve may be modified to contain a *Costus* extract or diosgenin derivative or epoxide. Drawing salve has been traditionally used to treat minor skin problems such as sebaceous cysts, boils, ingrown toenails and splinters. The main ingredients are often ichthammol, phenyl alcohol, or arnica montana, and may contain herbs such as *echinacea* or *calendula*.

Pastes included herein contain, in addition tc an ointment or cream base, high amounts of pulverulent constituents, such as zinc oxide, talc, starch or titanium dioxide. In one embodiment, the paste is selected from thegroup comprising fatty pastes or single-phase aqueous gels. The fatty paste includes petroleum jelly, hydrophilic petroleum jelly, or other similar compounds. The single-phase aqueous gel can incorporate carboxymethylcellulose or similar compounds. A paste may contain solid or encapsulated particles or emulsified and suspended particles containing a *Costus* extract or diosgenin derivative or epoxide.

Gels provided herein include semi-solid suspensions that contain a diosgenin epoxide extractor other *Costus* extract. The gels can be single- or two-phase systems. The gels can be oil or liquid based. Single-phase gels can contain small organic macromolecules distributed substantially uniformly throughout a liquid, such that the there is no boundary between the macromolecules and liquid. The liquid can be aqueous, but also contain an alcohol, and, optionally, an oil. Single-phase gels can be made from synthetic macromolecules or from natural gums. Two-phase gels can include a network of small, discrete particles. In one embodiment, two-phase gels are thixotropic. In one embodiment, the organic macromolecules include crosslinked acrylic acid polymers such as the "carbomer" family of polymers (i.e., carboxypolyalkylenes). The organic macromolecules can also be hydrophilic polymers such as polyethylene oxides, polyoxyethylene-polyoxypropylene copolymers and polyvinyl alcohol; cellulosic polyrriers such as hydroxypropyl cellulose, hydroxyethyl cellulose, hydroxypropyl methylcellulose, hydroxypropyl methylcellulose phthalate, and methyl cellulose; gums such as tragacanth and xanthan gum: sodium alginate; and gelatin. In another embodiment, the organic macromolecules having a stabilizing action include long-chain linear high molecular weight polysaccharides with a molecular weight of more than one million. In another embodiment, a uniform gel can be prepared by adding dispersing agents such as alcohol or glycerin. In another embodiment. the organic macromolecules can be dispersed by trituration, mechanical mixing or stirring, or combinations thereof. In another embodiment, the liquid can be either water or all water-miscible solvents. Examples of applicable solvents include alkanols, such as ethanol and isopropyl alcohol, benzyl alcohol, propylene glycol and similar solvents.

Hydrogels containing cross-linked insoluble starch or carboxymethylcellulose polymers and water and at least one component of the invention (e.g., a *Costus* extract or epoxidated diosgenin derivative), which may contain one or more ingredients according to the invention, may be applied to skin, a burn or a wound.

Hydrocolloid dressings containing polymers such as gelatin, pectin and cellulose and at least one ingredient according to the invention which form a waterproof adhesive dressing may be used to treat a skin disorder, burn or wound. For bacterial infections such as those associated with *Pseudomonas*, the pH may be kept low, for example, below pH 5, 6 or 7. Exudates produced by the wound are absorbed into the dressing and form a gel. Hydrocolloid dressings are capable of absorbing low to moderate levels of exudate and can be used to promote autolytic debridement of dry, sloughy, or necrotic wounds.

Alginate dressings containing at least one component according to the invention may also be used for skin disorders, burns or wounds. These tend to be highly absorbent and are available in two forms; calcium alginate and calcium sodium alginate. The use of alginate dressings as hemostatic agents was reported both in vitro and in clinical studies. The selection of an alginate dressing is usually to manage wound exudate, as it is claimed that they can absorb 15-20 times their own weight in wound fluid. The alginate forms a gel when it comes into contact with the wound surface. It can be used in granulating, epithelializing, and cavity wounds.

Other compositions suitable for incorporating a *Costus* extract or diosgenin derivative, especially for wounds such as diabetic ulcers, are described by Kavitha, et al., World J Diabetes. 2014 Aug. 15; 5(4): 546-556 which is incorporated by reference.

Aerosols as provided herein include products packaged under pressure and contain ingredients that are released upon activation of an appropriate valve system. Aerosols include all self-contained pressurized products, such as fine mists of spray or foam. that are emitted from a pressurized container containing a propellant, foams, or semisolid liquids. They may also be emitted by an unpressurized atomizer that is pressurized by a hand-operated pump rather than by stored propellant. In one embodiment, the aerosol comprises a container, a propellant, a concentrate containing an active ingredient, a valve (which may be a metered valve), and an actuator. The nature of these components determines characteristics such as delivery rate, foam density, and fluid viscosity. In another embodiment, the aerosol is a two-phase formulation comprising a gas and liquid. In another embodiment, the aerosol is a three-phase formulation comprising a gas, liquid, and suspension or emulsion of active ingredients. In this formulation, suitable excipients, such as netting agents and/or solid carriers such as talc or colloidal silicas are included. In another embodiment, the propellant is liquefied or vaporized. In another embodiment, a solvent can be the propellant or a mixture of the propellant and co-solvents such as alcohol and polyethylene glycols. In another embodiment, the propellant is selected from the group comprising a spray, foam, or quick-breaking foam. In another embodiment, spray formulations are aqueous solutions n a container having a spray means such as an atomizer or nebulizer. An aerosol may contain solid or encapsulated particles, emulsified acid suspended particles, or liquid or atomized droplets containing a *Costus* extract or diosgenin derivative or epoxide.

Foams. In some embodiments, a *Costus* extract or diosgenin derivative or epoxide is delivered to the body while in a foam state, such as stable foam, for example, that is produced with or without a propellant. For example, the extract may be contained in a shaving foaan and used for preventing bacterial infection of nicks, cuts or abrasions associated with shaving. In some versions, a foam is dispensed from a dispenser such as a propellant-free dispenser with pumping action to create the foam from a composition in a foamable carrier, and then applied to a wipe or other substrate, or applied to the hand of the user or otherwise delivered to the skin. Propellant-driving foam generators may also be used to deliver the composition in the form of a foam. Active ingredients in a foamfoatra rraay be dispensed for subsequent placement on a dry wipe, a pre-moistened wipe, or other soft, flexible applicator (e.g., an object about 3-fingers wide or 4 to 10 cm wide) or other object to be used for application of the foam-based composition to the skin. The foam can be a non-propellant foam. A foam with a suitable stiffness of yield stress can be applied to the skin in any manner for sustained adherence and contact with the body. Examples of foam-based systems are described in U.S. Pat. No. 6,818,204, "Stable Foam for Use in Disposable Wipe," issued to Lapidus on Nov. 16, 2004, herein incorporated by reference. The Lapidus patent involves the use of compatible surfactants, e.g., nonionic, anionic, amphoteric, for use in human hygienic products. The surfactant should be capable of forming a tbam when mixed with air in a finger actuated, mechanical pump foamer. Such surfactants are said to include, without limitation, those which do not irritate mucous membranes such as polyethylene 20 cetyl ether (Brij 58)™, a nonionic surfactant; sodium lauroyl sarcosmate (Hamposyl L-30)™, sodium lauryl sulfoacetate (Lathanol LAL)™ and sodium laureth sulfate (Sipon ESY)™, anionic surfactants; lauramidopropyl betaine (Monateric LMAB™), an amphoteric surfactant, as well as polysorbate 20, TEA-cocoyl glutamate, disodium cocoamphodiacetate and combinations thereof. Typically, a surfactant is present in an amount from about 2% to about 35% by weight, or from about 5% to about 15% by weight (or any intermediate value or subrange).

At least one foam stabilizing agent may be present in some foamable embodiments. Suitable foam stabilizing agents may include, without limitation, natural or synthetic gums such as xanthan gum, polyalkylene glycols such as polyethylene glycol, alkylene polyols such as glycerine and propylene glycol and combinations thereof. Typically, the foam stabilizers may be present in an amount from about 0.10% to about 5%, or from about 2% to about 4%. In the Lapidus patent (U.S. Pat. No. 6,818,204), alkylene polyols are said to be typically employed in amounts from about 0.1% to about 10%, gums are employed inamountsranging from about 0.05% to about 1%, and/or polyalkylene glycols are present in aanounts ranging from about 0.05% to about 2%. The ranges above include all intermediate values and subranges.

A foam may be produced using the F2 Finger Pump Foamer™. manufactured by AirSpray International Inc. of Pompano Beach, Fla. Such a spring-loaded valve system operates without the use of gas propellants or the like. Upon actuation, precise amounts of air and liquid are mixed, and a foam capable of maintaining its structure fora substantial length of time is dispensed. In addition, the dispenser can deliver a variable amount of foam, thereby reducing waste of the wipe agent contained therein. Details of exemplary propellantless defoamers are described in U.S. Pat. No. 5,443,569, issued on Aug. 22, 1995, and U.S. Pat. No. 5,813,576, issued Sep. 29, 1998, herein incorporated by reference.

Encapsulation. The *Costus* extracts and diosgenin derivatives described herein can be encapsulated in a c rier such as in liposomes, micelles, or microspheres. Suitable carriers are described in U.S. Pat. No. 7,205 003, hereby incorporated by reference.

Micelles provided herein can comprise surfactant molecules arranged such that their polar head groups form an outer spherical shell, while their hydrophobic, hydrocarbon chains are oriented towards the center of the sphere, forming a core. The precursor and agent (e.g., *Costus* extracts and diosgenin derivatives) are encapsulated ithin the core of the micelle. Surfacta suitable for foritaing micelles include, but are not limited to, potassium laurate, sodium octane sulfonate. sodium decane sulfonate, sodium dodecane sulfonate, sodium lauryl sulfate. docusate sodium, decyltrimethylammonium bromide, dodecyltrimethylammonium bromide, tetradecyltrimethylammonium bromide, tetradecyltrimethyl-ammonium chloride, dodecylammonium chloride, polyoxyl-8 dodecyl ether, polyoxyl-12 dodecyl ether, nonoxynol 10, and nonoxynol 30.

Liposomes provided herein are microscopic vesicles having a lipid wall comprising a lipid bilayer. Liposomal preparations herein include cationic (positively charged), anionic (negatively charged), and neutral preparations including the *Costus* extracts and diosgenin derivatives. Cationic liposomes include N[1-2,3-dioleyloxy)propyl]-N, N,N-triethylammonium (DOTMA). Anionic and neutral liposomes can be easily prepared using materials such as phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE). These materials can also be mixed with DOTMA in appropriate ratios.

Microspheres provided herein can comprise micro- or nano-scale carriers that are made of polymers, both synthetic and natural and which contain the *Costus* extracts and diosgenin derivatives. Additional nomenclature describing microspheres include, but are not limited to, spheres, beads, particles, carriers, microbeads, microparticles, microcarriers, nanospheres, nanobeads, nanoparticles, and nanocarriers.

Polymeric materials suitable for the microspheres provided herein include those that are described in U.S. Pat. No. 6,423,345, hereby incorporated by reference in its entirety for all purposes, including poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes poly(vinyl alcohols), poly(vinyl acetate), polystyrene, polyurethanes and co-polymers thereof, derivativized celluloses such as alkyl cellulose hydroxyalkyl cellulcses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium, polymers of acrylic acid, methacrylic acid or copolymers or derivatives thereof including esters, poly(methyl methacrylate), poly(ethyl methacrylate), poly(butylmethacrylate), poly(isobratyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups, for example, alkyl, alkylene, hydroxylations, oxidations, and other modifications routinely made by those skilled in the art. Natural polymers including agarose and alginate are also suitable for the microspheres. Any of the above carriers can include proteins, lectins, and other biological materials The precursors and activating agents can he encapsulated into the carriers using known techniques in the art, including microspheres described in U.S. Pat. No. 6,423,345, incorporated by reference, including solvent evaporation, hot melt microencapsulation, solvent removal. and spray drying of microspheres. In one embodiment, the microsphere comprises a block copolymer. In another embodiment, the microsphere comprises a hydrogel.

Sustained-release formulations may be prepared. Suitable examples of sustained-release preparations include semipermeable matrices of solid hydrophobic polymers containing the desired antifungal agents. The matrices may be in the form of shaped articles, e.g., films, or microcapsules. Examples of sustained-release matrices include polyesters, hydrogels (for example, poly(2-hydroxyethyl-methacrylate), or poly(vinylalcohol)), polylactides (see U.S. Pat. No. 3,773,919), copolymers of L-glutamic acid and ethyl-L-glutamate, non-degradable ethylene-vinyl acetate, and degradable lactic acid-glycolic acid copolymers such as the LUPRON DEPOT™ (injectable microspheres composed of lactic acid-glycolic acid copolymer and leuprolide acetate). Compositions useful herein may be adapted for immediate, delayed, modified, sustained, pulsed or controlled release of a compound of the invention. For example, a wound dressing or composition applied to the skin, hair or nails may be formulated to release the active compounds over a period of 1-24 hours or 1-14 days (e.g., where skin or a treatment site is substantially immobilized nts immobilized in a bed or covered by a cast, bandage, etc.) or any intermediate period of time Suppositories. In addition to the active *Costus* extracts and diosgenin derivatives, a suppository may contain the customary water-soluble or water-insoluble excipients, for example polyethylene glycols, fats, for example cocoa fat and higher esters (e.g., $C_{14}$-alcohol with $C_{16}$-fatty acid) or mixtures of these substances.

Tablets, Capsules, Pills. In some embodiments, the *Costus* extracts or diosgenin derivatives will be formulated as a tablet, capsule or pill. These may contain the customary excipients, such as fillers and extenders for example starches, lactose, sucrose, glucose, mannitol, and silicic acid; binders, for example carboxymethyl cellulose, alginates, gelatin, polyvinylpyrrolidone; humectants, for example glycerin; disintegrating agents, for example agar-agar, calcium carbonate and sodium carbonate; dissolution retardants, for example paraffin; resorption accelerating agents, for example quaternary ammonium compounds; wetting agents, for example cetyl alcohol, glycerol monostearate; adsorption agents, for example kaolin and bentonite; and lubricants, for example talcum, calcium stearate and magnesium stearate, and solid polyethylene glycols or mixtures of the substances mentioned above. In some embodiments, the active ingredient(s) can be in a microencapsulated form in the tablet or capsule, which can optionally be foimulated to release the active Diosgenin epoxide component at a particular location within the GI tract, e.g, to transit the stomach and release the active component n the small or large intestine.

Capsules can contain any standard pharmaceutically acceptable materials such as gelatin or cellulose. Tablets can be formulated in accordance with conventional procedures by compressing mixtures of the active ingredients with a solid carrier and a lubricant. Examples of solid carriers include starch and sugar bentonite. Active ingredients can also be administered in a form of a hard shell tablet or a capsule containing a binder, e.g., lactose or mannitol, a conventional filler, and a tabletting agent.

Powders may be formulated to contain dry or encapsulated *Costus* extract or diosgenin derivative and the customary excipients, for example lactose, talcum, silicic acid, aluminum hydroxide, calcium silicate, and polyamide powder, or mixtures of these substances. Such powders may be formulated for topical application or for inhalation.

Personal care Products mar be formulated to contain a *Costus* extract or diosgenin derivative. These may be used as preventative care products to prevent ring worm and other skin infections or as deodorants r personal care products that prevent the formation of body odors or rough skin such as those produced by the growth of microbes in or on the skin. The diosgenin, diosgenin epoxide or *Costus* extract may be incorporated into conventional body washes, lotions, lubricants, personal care composition, antiperspirants, or deodorants. Such products are well known in the art and commercially available and are also described by Broad, U.S. Pat. No. 4.252,789, which is incorporated by reference, especially for their descriptions of conventional deodorant ingredients, formulations, and modes of use. These products can be applied to the axilla, inguinal region, feet or other odor-producing, moist or intertriginous or interdigital body part to prevent growth of odor-causing microorganisms. In other embodiments, the extract of the invention can be incorporated into a deodorizer, cleaner, or disinfectant such as a liquid sanitizer or disinfectant, a spray or wipe for cleaning surfaces exposed to bacterial contaminants.

Other personal care products include cosmetic compositions such as nail care compositions such as nail (finger and toe) polish and nail polish removers, and makeup products that contain a color deposited onto a keratinous substrate such as skin, lips, and lashes. Makeup products include primers, lipstick, lip gloss, lip plumper, lip liners, lip balms, eyeliners, eyeshadows, masara, concealers, rouges, foundations, face powders, highlighters, contour powders or creams, bronzers, eyebrow definers, and setting sprays for makeup. A cosmetic composition can be in many different forms, including liquid or cream emulsions; powders that are pressed, cast, or loose; dispersions, and anhydrous creams or sticks; or solids such as pencils and the aforementioned powders and sticks; shower and bath compositions containing the liphophilic hydroxytyrosol carbonate ester compounds include but are not limited to body washes (including moisturizing body wash), shower gels, skin cleansers, cleansing milks, in shower body moisturizer, and pet shampoo; hair care compositions include shampoos, hair conditioners, colorants, dyes, bleaches, straighteners, and permanent wave products; infant care compositions include infant shampoo, infant body wash, and infant bubble bath; skin care compositions include shaving compositions, cleansing compositions, emollients, moisturizing compositions including anti-aging compositions; exfoliant compositions, face masks, and skin toners, and compositions containing pharmaceutically active ingredients for reduction of skin irritations, rashes, inflammations, and excema; and sun care compositions including compositions containing UV blocking agents (UVA and/or UVB), such as sun tan compositions, sunscreen compositions having an SPF rating of 20 or more, or 30 or more, or 40 or more, or 50 or more; and lip balms and lip care for protection against wind and sun. Sun care compositions may also include sunless tanning treatments.

A personal care composition may be in any of the forms described above including in the form of lotions, oils, creams, gels, and sprays. A personal care composition may contain carriers, cleansing agents, emollients, moisturizers or hydrating agents, active anti-aging or anti-wrinkle agents, pigments, colorants, fragrances, biocides, preservatives, antioxidants, antiperspirant agents, exfoliants, hormones, enzymes, medicinal compounds, vitamins, ultraviolet light absorbers, skin bleaching agents, anti-acne agents, botanical extracts, silicone ohs, organic oils, waxes, adhesion promoters, plasticizers, film formers, including hair fixatives, thickening agents, fillers and binders, alcohol and other organic solvents, and propellants.

Parenteral formulations acid dosage forms include aqueous solutions, isotonic saline or glucose solutions comprising the active agent, or other well-known pharmaceutically acceptable carriers. Solubilising agents well-known to those familiar with the art can be used as pharmaceutical excipients. Injectable-dosage forms may be formulated as liquid solutions or suspensions. Solid forms suitable for solution in, or suspension in, liquid prior to injection may also be prepared.

Cleaning Agent/Disinfectant. A composition containing diosgenin, diosgenin epoxide or *Costus* extract may be formulated for use as a cleaning or disinfecting agent, such as a hard surface cleaning, product. Dermatophytes and bacteria are often transmitted via exposure to water ire, a shower, bath, hot tub or other facilities at a spa or gym. It may further contain cleaning agents, such as chelators or surfactants, which do not interfere with the antimicrobial activity of the diosgenin, diosgenin epoxide or *Costus* extract. The formulation of such a cleaning or disinfecting solution and inclusion of general cleaning agents can easily be done by a skilled artisan and the stability and effectiveness of the solution san be easily tested by the skilled artisan.

The term "hard surface cleaning composition" refers to a composition that is used to clean and/or sanitize a hard or solid surface. In one embodiment, the invention provides a compositionthat prevents or removes microbial growth on hard surfaces including, but not limited to, walls, floors, countertops, sinks, toilets, showers, bathtubs, hot tubs saunas, benches, lockers, kitchen, bathroom and locker room surfaces, airline, bus and transport surfaces, entry and exit doors, railings, escalator or elevator surfaces, drip irrigation components, water filtration units, medical or athletic instruments and equipment, and the like.

Foods, Beverages & Feeds. In other embodiments, a composition containing diosgenin, epoxidated diosgenin or derivatives thereof or a *Costus* extract is formulated as an ingestible food or beverage. These components of the invention may be incorporated into animal feeds for mammals (cattle, sheep, goats etc.), birds (e.g., chickens, turkeys, quail, ducks, geese, hawks, falcons, etc.), fish (e.g., tilapia, carp, catfish, salmon, trout, aqua cultured fish, etc.), and crustaceans (e.g., shrimp, lobsters, etc.), mollusks (e.g., abalone, oysters, clams, mussels, etc.). In some embodiments, an active ingredient of the invention will be incorporated into a liquid medium in which an animal is grown, e.g., into a medium for aquaculture. In other embodiments, the extract may be encapsulated in a form that permits uptake by an animal, for example, in an encapsulated particulate form that can be ingested by fish.

Agriculture. In some embodiments, diosgenin, diosgenin epoxide or *Costus* extract of the invention can be applied to control the growth of yeasts, fungi or bacteria in or on plants, such those causing leaf spots, rots, scabs, and wilting. It may be sprayed or otherwise applied to the roots, foliage, flowers or seeds of a plant. It may be added to culture medium used for hydroponic cultivation of plants.

The efficacy of a composition useful herein can be evaluated both in vitro and in vivo. See, e.g., the examples below. Briefly, in one embodiment the composition can be tested for its ability, to for example, inhibit fungal, yeast, or bacterial growth in vitro. For in vivo studies, the composition can be administered town animal (e.g., a mouse) and its effects on fungal infection, or one or more symptoms of the fungal disease or disorder are then assessed. Based on the results, an appropriate dosage range, frequency, and administration route can be determined.

It should be understood that the additional agents listed above may also be employed in a method of the invention where they are administered separately, simultaneously or sequentially with a compound, isolate or composition useful herein.

As will be appreciated, the dose of the composition administered, the period of administration, and the general administration regime may differ between subjects depending on such variables as the severity of symptoms of a subject. the of disorder to be treated, the mode of administration chosen, and the age, sex and/or general health of a subject. However, by way of general example, from about 1 µg to about 5,000 mg per kg body weight, about 1 mg to about 4,000 mg per kg body weight, about 1 mg to about 3,000 mg per kg, body weight, about 1 mg to about 2,000 mg per kg body weight, about 1 mg to about 1,000 mg per kg body weight, or about 1 mg to about 500 mg per kg body weight of a compound useful herein is administered, per administration or per day, preferably about 50 to about 1,000 mg per kg, preferably per day. Administration may include a single dose, such as a single daily dose, or administration of a number of discrete divided doses as may be appropriate. A person of ordinary skill in the art will be able to determine without undue experimentation, having regard to that skill and this disclosure, an effective dosage regime (including dose and timing of administration) for a given condition.

When used in combination with an additional agent, the administration of a compound useful herein and the other agent may be separate, simultaneous or sequential. Simultaneous administration includes the administration of a single dosage form that comprises all components or the administration of separate dosage forms at substantially the same time. Separate or sequential administration includes administration according to different schedules, preferably so that there is an overlap in the periods during which the composition useful herein and other therapeutic agent are provided.

Additionally, it is contemplated that a composition in accordance with the invention may be formulated with additional active ingredients which may be of benefit to a subject in particular instances. For example, therapeutic agents that target the same or different facets of the disease process may be used.

The compounds or compositions of the invention may be incorporated into or onto medical devices and medical supplies. The medical devices or supplies may be coated or impregnated with compositions of the invention by known methods.

Nonlimiting embodiments of the invention include the following.

Embodiment 1: A method tbr inhibiting the growth of at least one microorganism comprising contacting it with a *Costus speciosis* extract comprising epoxidized diosgenin, wherein said at least one microorganism is *Microsporum, Candida, Pseudomonas* or *Staphylococcus*. In some embodiments, the method may be practiced using epoxidized diosgenin or a derivative thereof from a non-*Costus* source, such as that isolated from another plant source or prepared by chemical synthesis. Isolated or purified diosgenin or epoxidated diosgenin may be added to an extract according to the invention, such as to a methanol, ethanol, water, chloroform or essential oil extract of *Costus speciosis*. For example, an inhibitory or cidal amount of epoxidated diosgenin or extract treated to contain diosgenin may be combined with an inhibitory or cidal amount of a methanol or ethanol extract of *Costus* roots to expand the spectrum of microbial infections treated or to reduce the relative amounts of each active ingredient. In other embodiments, the method may be practiced with one or both of a methanol or ethanol extract of *Costus*.

Embodiment 2. The method of embodiment 1, further comprising contacting the at least one microorganism with an essential oil extract of *Costus speciosis*.

Embodiment 3. The method of embodiment 1, further comprising contacting the at least one microorganism with a methanol extract of *Costus speciosis*.

Embodiment 4. The method of embodiment 1, further comprising contacting the at least one microorganism with an ethanol extract of *Costus speciosis*.

Embodiment 5: The method of embodiment 1, wherein the at least one microorganism is *Microsporum*.

Embodiment 6: The method of embodiment 1, wherein the at least one microorganism is *Candida*.

Embodiment 7. The method of embodiment 1, wherein the at least one microorganism comprises *M. gypsum, M. tropicalis, M. canis* or *C. albicans*.

Embodiment 8: The method of embodiment 1, wherein the at least one microorganism is *Pseudomonas aeruginosa*.

Embodiment 9: The method of embodiment 1, wherein the at least one microorganism is *Pseudomonas* or *Staphylococcus aureus*.

Embodiment 10. The method of embodiment 1, wherein the at least one microorganism is in the skin, hair or nails of a subject having *tinea*. Subjects having tinea include those having *tinea capitis* or *tinea barbae, tinea unguium* or onychomycosis; subjects having *tinea manuum, tinea corporis, tinea faciei* or *tinea cruris*; and subjects having *tinea pedis* or athlete's foot.

Embodiment 11. The method of Embodiment 1, wherein the at least one microorganism is associated with a sinus or respiratory infection.

Embodiment 12. The method of Embodiment 1, wherein the at least one microorganism is associated with a burn, wound or skin or mucous membrane infection.

Embodiment 13. The method of Embodiment 1, wherein the at least one microorganism is in a diabetic ulcer or wound.

Embodiment 14. The method of Embodiment 1, wherein the *Costus speciosis* extract comprises *Costus* components soluble in methanol and epoxidized diosgenin.

Embodiment 15. The method of Embodiment 1. wherein the *Costus speciosis* extract comprises *Costus* components soluble in ethanol and epoxidized diosgenin.

Embodiment 16. The method of Embodiment 1, wherein the *Costus speciosis* extract comprises substantially pure epoxidized diosgenin.

Embodiment 17. The method of Embodiment 1 that comprises topically administering a composition containing at least 1 wt % of *Costus* extract containing epoxidized disgenin to a subject in need thereof.

Embodiment 18. The method of embodiment 1, wherein the at least one microorganism is associated with a sinus or respiratory infection.

Embodiment 19. The method of embodiment 1 wherein the at least one microorganism is associated with a burn, wound or skin or mucous membrane infection.

Embodiment 20. The method of embodiment 1, wherein the at least one microorganism is in a diabetic ulcer or wound.

Embodiment 21. A method for producing a *Costus speciosis* extract comprising epoxidized diosgenin comprising extracting roots of *Costus speciosis* with methanol, ethanol, or other solvent, recovering the material that dissolves in the solvent, and treating it with m-chloroperbenzoic acid to yield a *Costus speciosis* extract containing diosgenin epoxide. Extracts may be made using an extraction solvent that contains from >0 to 100% of a particular solvent, such as water, methanol, ethanol, another C1-C6 alcohol, chloroform or other organic solvent. Preferably, the amount of the particular solvent will range from at least 50, 60, 70, 80, or 90% of the extraction solvent, more preferably fro 80-100 of the extracting solvent, though these ranges include all intermediate values and subranges. Extracts may be prepares at a pH ranging from 1 to 10, preferably, from 5-8 or any intermediate pH value and at a temperature where the solvent remains liquid or gaseous, for example, from 0 to 100° C.

Embodiment 22. A composition comprising a *Costus speciosis* extract obtained by the method of embodiment 21 and optionally a phaimaceutically acceptable carrier or excipient.

Embodiment 23. The composition of embodiment 22 in combination with at least one water treatment, soap, detergent, or disinfectant.

Embodiment 24. A method for inhibiting microbial growth comprising contacting *M. gypsum, M. canis* or *C. albicans* with essential oil, an ethanol extract, or a methanol extract of *Costus speciosis*.

Embodiment 25. A method for inhibiting microbial growth comprising contacting *Pseudomonas aeruginosa* or *Staphylococcus aureus* with essential oil, an ethanol extract, or a methanol extract of *Costus speciosis*.

Embodiment 26. A method for inhibiting microbial growth comprising contacting *M. gypsum, M. canis* or *C. albicans* with a *Costus speciosis* extract comprising epoxidated diosgenin.

Various aspects of the invention will now be illustrated in non-limiting ways by reference to the following examples.

EXAMPLE

The following examples illustrate various aspects of the present invention. They are not to be construed to limit the claims in any manner whatsoever.

The inventors sought to identify *Costus* extracts exhibiting antimicrobial effects on dermatophytes and other dermal nmicrobes. A dried fine powder of Indian *Costus* plant roots was used to prepare extracts. Epoxidation of diosgenin wvas performed by using m-chloroperbenzoic acid. The extracts, essential oil, diosgenin were tested for their antimicrobial activity. After treatment with essential oil extract, the change in the general shape of the fungal spores was examined by SEM analysis Material and Methods Chemistry. IR spectra were performed on a Perkin-Elmer 16 FPC FT-IR spectrophotometer as thin films. 1HNMR and 13CNMR spectra were obtained in $CDCl_3$ solution with a Bruker AVANCE D.P.X. 600 MHz apparatus. GC-MS wwFere determined by Joel JMS 600H, GC Hewlett Packerd, HP 6890 Series, with a capillary column (30 m. 0.32 nm, 0.25 ml) HP-5 cross linked 5% dimethyl polysiloxane. The change in the general shape of the fungal spores after treatment with essential oil extract was examined with Scanning Electron Microscopy in King Fand Center for Medical Research-King Abdulaziz University-Jeddah, Saudi Arabia. Thin layer chromatography (TLC) and Preparative Layer Chromatography (PLC) were done by Polygram SIL G/W 254, Mecherey-Nagel. A rotator evaporator (at 20° C./15 ton) was used to remove the solvents.

Plant material. The dried roots of Indian *Costus* were collected from herb store (Jeddah, Saudi Arabia). All the roots were washed with water, dried and ground well. The fine powder obtained gas used to extract the essential oil and this oil was tested for its antimicrobial activity; Ody P. *The herb society's complete medicinial herbal.* Translation: Elvira Academic International 1999; 118-120 (incorporated by reference).

Extraction of essential oil. The dried root fine powder (550 g) of Indian *Costus* was subjected to steam distillation for three hours. About 50 mL of the distillates were collected and extracted with chloroform (3×100 mL). The extracts were dried over anhydrous sodium sulphate (Merck, Germany), and the solvent was removed by evaporation. The essential oil yield obtained was around 0.65 wt % and was stored, in a refrigerator at 6° C.

Preparation of plant extracts. The dried powdered roots of Indian *Costus* (200 g) were extracted successively using cold percolation system of ethanol, methanol, distilled water or chloroform (400 ml for each) for 4 days, using a stirring apparatus; Duraipandiyan V, Ignacimuthu S. *Antibacterial and antifungal activity of Flindersine isolated from Toddalia asiatica (L) Lam. A traditional medicinal plant.* J Ethnopharmacol 2009; 123: 494-498 (incorporated by reference). The solutions collected were filtered through Whatman filter paper. The extracts were evaporated to dryness under reduced pressure at 90° C. by Rotary vacuum evaporator to obtain the respective extracts and stored under liquid nitrogen.

General epoxidation procedure of natural steroids using m-chloroperbenaoic acid. A solution of m-CPBA (10 mmol, 80%) was added cautiously drop wise over 15 min to a stirred solution 1 (5 mmol) in $CHCl_3$ (25 ml) at 0° C. The mixtures were stirred continuously in an atmospheric nitrogen at room temperature (TLC, peroxide test by KI, 10%), after which it was, carefully washed with a saturated aqueous solution of $NaHCO_3$ (3×10 ml) followed by distilled water (3×10 ml). The organic layers were separated, dried over anhydrous $Na_2SO_4$ and evaporated under reduced pressure at room temperature. The crude residue products were purified by column chromatography on silica gel adsorbent. Elution of the column was performed with the solvent mixture of petroleum ether 60-80° C. and ether (9:2), which gave the epoxide product 2a,b.

Diosgenin (1) (3β,25R)-spirost-5-en-3-ol): Colorless crystal, mp: 204-206° C., C27H42O3 (M. wt., 414.6). IR (KBr) cm-1: 3417 (br, OH), 2933 (CH, s), 1602 (C=C), 1169 (C—O). 1HNMR (CDCl3): δ 0.79 (d, 3H, J=6 Hz, H-27), 0.80 (s, 3H, H-18), 0.98 (d, 3H, J=7 Hz, H-21), 1.02 (s, 3H, CH-19), 2.34 (comp. pat., 2H, H-7) 3.38 (dd, 1H, J=11 Hz, H-26), 3.47 (dd, 1H, J=11, 4 Hz, H-26), 3.52 (comp. pat., 1H, H-3), 4.42 (dd, 1H, J=11, 7 Hz, H-16), 5.38(d, 1H, J=5 Hz, H-6), 0.79-2.31 (comp. pat., remaining protons). 13C-NMR, DEPT (CDCl3) δ 14.5 (C21), 16.3

Figure 2:
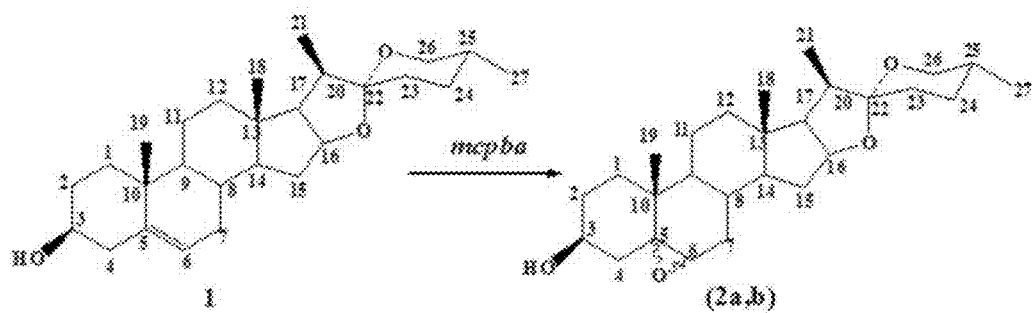
FIG. 2. Epoxidation of diosgenin.

(C27), 17.2 (C19), 19.4 (C18), 20.9 (C11), 28.8 (C15), 30.3 (C8), 31.4 (C25), 31.5 (C24), 31.6 (C7), 31.9 (C12), 32.1 (C1), 36.7 (C13), 37.2 (C23), 39.8 (C2), 40.3 (C1°), 41.6 (C2°), 42.3 (C4), 50.1 (C14), 56.5 (C9), 61.9 (C17), 66.9 (C26), 71.8 (C3), 80.8 (C16), 111.9 (C22), 121.4 (C6), 140.8 (C5). MS: m/z 414 (M+, C27H42O3, 3%), 353 (M+-C3H9O, 3%), 342 (M+-C4H8O, 8%), 300 (M+C6H10O2, 11%), 267 (M+-C8H19O2, 12%), 139 (C9H15O, 100%). See FIG. 2.

5,6-Epoxyspirostane (2a,b): Colorless crystal, mp: 195-200° C., C27H42O4 (M. wt., 430.6). IR (KBr) cm-1: 3383 (br, OH). 2926, 2869(CH, s), 1601 (C═C), 1101 (C—O). MS: m/z, 430 (M+, C27H42O4, 5%), 358(C24H38O2, 10%) 325 (C22H29O2, 5%), 139 (C9H15O, 100%). See FIG. 2.

Exo form 2a (5α,6α-Epoxyspirostane): 1H-NMR (CDCl3): δ 0.75 (s, 3H, H-18), 0.81 (d, 3H, J=6 Hz, H-27), 0.98 (d, 3H, J=7 Hz, H-21), 1.1 (s, 3H, H-19), 2.93 (d, 1H, J=4 Hz, H-6) 3.38 (dd, 1H, J=11 Hz, H-26), 3.5 (dd, 1H, J=11, 3 Hz, H-26), 3.93 (comp. pat., 1H. H-3), 4.41 (dd, 1H, J=7.5 Hz, H-16), 0.71-2.11 (comp. pat., remaining protons). 13C-NMR, (CDCl3): δ 14.5 (C21), 16.3 (C27), 17.2 (C19), 19.4 (C18), 20.8 (C11). 28.8 (C15). 30.3 (C8). 31.4 (C25), 31.4 (C24). 31.6 (C7), 31.8 (C12), 32.2 (C1), 36.6 (C13), 37.2 (C23), 39.9 (C2), 40.4 (C1°), 42.1 (C17), 42.3 (C4), 41.6 (C2°), 50.0 (C14), 56.5 (C9), 61.8 (C6), 62.1 (C16), 65.2 (C3), 669 (C26), 71.7 (C5), 111.8 (C22).

Endo form 2b (5β,6β-Epoxyspirostane): 1H-NMR (CDCl3): δ 3.11 (d, 1H, J=4 Hz, H-6), 4.26 (comp. pat., 1H, H-3), remaining protons appeared as 2a. 13C-NMR (CDCl3): δ14.4 (C21), 16.2 (C27), 17.2 (C19), 19.4 (C18), 20.6 (C11), 28.8 (C15), 30.3 (C8), 31.4 (C25), 31.4 (C24), 31.6 (C7), 31.8 (C12), 32.2 (C1), 36.0 (C13), 37.2 (C23), 40.0 (C2), 40.4 (C1°), 42.1 (C17), 42.3 (C4), 41.6 (C2°) 50.1 (C14), 56.6 (C9), 61.9 (C6), 62.2 (C16), 65.2 (C3), 66.9 (C26), 71.6 (C5), 111.8 (C22).

Determination of Antimicrobial Activities

*M. gypseum, M. canis, C. albicans* and *C. tropicalis* isolates were obtained from King Faisal Specialist Hospital & Research Centre-Jeddah, Saudi Arabia. They were cultured on sabaroud dextrose agar media (Oxoid CM 41) at 25° C.

Pathogenic bacteria *P. aeruginosa* and *S. aureus* were obtained from King Faisal Specialist Hospital & Research, Centre-Jeddah, Saudi Arabia. A blood agar a medium (Oxoid) was used for cultivation of pathogenic bacteria at 37° C.; see Madigan M, Martinko J. Brock *Biology of microorganisms*, 11th ed. Prentice Hall. ISBN 2005; 0131443291 (incorporated by reference).

Antimicrobial activities of essential oils and plant extracts of Indian *Costus*. About 0.5 g of the testing compound was dissolved in 1.25 ml of a solvent (chloroform, ethanol and methanol) and it was cultured in sabaroud dextrose agar media and blood agar media using the agar disc diffusion method. Each media used were inoculated with 1 ml from a suspension of *M. gypseum, M. canis* and *C. albicans* for sabaroud dextrose agar and *P. aeruginosa* and *S. aureus* for blood agar. The fungi and yeast were incubated at 25° C. for 8 days, and 48 hours respectively and then tested at 37° C. for 24 hours. After that, the diameter of inhibition zones was measured in millimeters; Baker F J, Breach M R. *Medical Microbiological Techniques*, Butterworths 1980; Hasenekoglu H. *Laboratory techniques for micro fungi*. Ataturk University. Erzurum 1990 (both incorporated by reference).

Analysis of Results. The curative properties of medicinal plants are perhaps due to the presence of various secondary metabolites such as alkaloids, flavonoids, glycosides, phenols, saponins, sterols etc. The extracts of rhizome have revealed the presence of alkaloids, flavonoids, cardiac glycosides, saponins, sterols and tannins, which may have led to their discovery and development as drugs; Saraf *A. Phytochemical and Antimicrobial Studies of Medicinal Plant Costns speciosus (Koen.)*. E J Chem 2010; 7: S405-S413. The pharmacological action of crude extract is determined by the nature of their constituents; Mukherjee P K. Quality *Control of Herbal Drugs, an approach to evaluation of botanicals*. 1st ed. Business Horizons 2002; New Delhi. The aqueous extract of *Costus speciosus* rhizomes showed antimicrobial activity against *Staphylococcus aureus*. However, the organic phase (e.g. methanolic extract) did not show inhibitory activity against any bacteria, Saraf et al., (2010) id. The steroidal sapogenins diosgenin (1) has been successfully isolated from *C. specious* (Koen) rhizome extract and identified with authentic samples by comparison of spectroscopic data.

The epoxidation of diosgenin (1) using m-chloroperbenzoic acid (m-CPBA) at room temperature gave the regioisomeric 5α,6α-epoxyspirostane and 5β,6β-epoxyspirostane (2a,b) (exo1H-NMR spectrum of 2a showed doublet of doublet at δ 2.9 for H-6 which was shifted from δ 5.36 of starting 1. 13C-NMR s ectruira of 2a showed signals at δ 71.7 and 61.9 for carbons in positions 5 and 6. 1H-NMR spectrum of 2b showed doublet at δ 3.11 for H-6 and complex pattern at 4.21 for H-3. 13C NMR spectrum of 2b showed signals at δ 71.6 and 61.9 for carbons in positions 5 and 6 which were shifted from 140.8 and 121.4 of the same carbons of the start 1. MS spectrum of 2a showed molecular ion at m/z 430 for its molecular weight.

Figure 3:
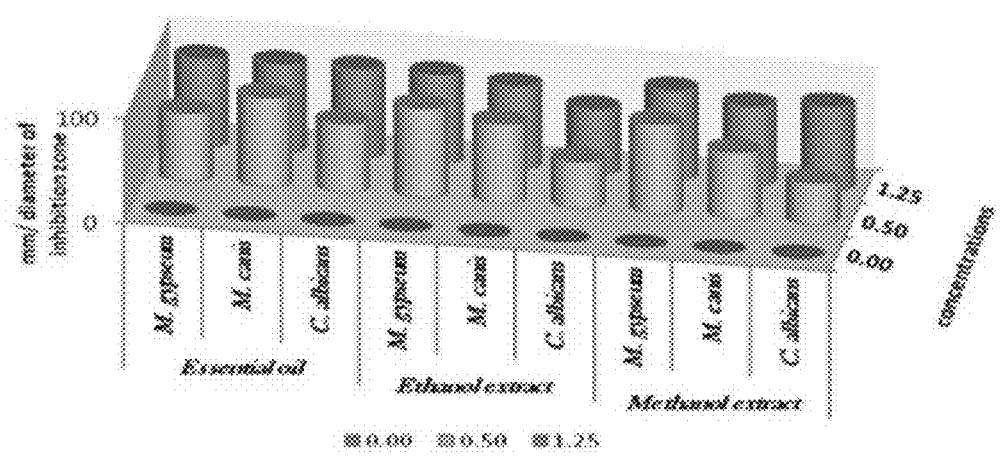
FIG. 3. Effect of various concentrations of Indian *Costus* extracts against *M. gypseum, M. canis* and *C. albicans* grown on sabaroud dextrosemedia (mm/diameter of inhibition zone).

The antimicrobial activities of Indian *Costus* extracts were tested on fungi, yeast and bacteria. The results (FIG. 3) showed high inhibition of *M. gypseum, M. canis* and *C. albicans*. The treatment by oil extract showed an inhibitory effect on the fungi with methanol and ethanol extracts. At 1.25 m the inhibition zone vas 85 mm of essential oil, (85, 75 and 80 mm) of methanol extract and (85, 79 and 62 mm) of ethanol extract respectively. In addition, *M. gypseum* growth was more sensitive than *M. canis* and *C. albicans* at 1.25 m of all extracts compared to the control sample.

Figure 4A:
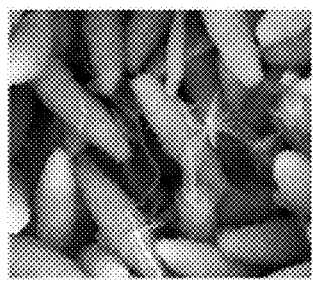
FIGS. 4A-4C. SEM images of *M. gypseum* (control) showing the normal growth of spores and hyphae.
Figure 4B:
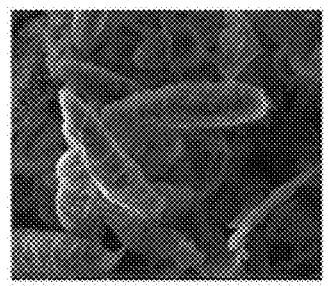
Figure 4C:
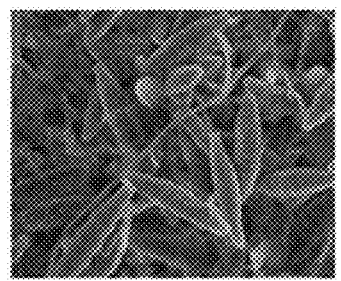
Figure 5A:
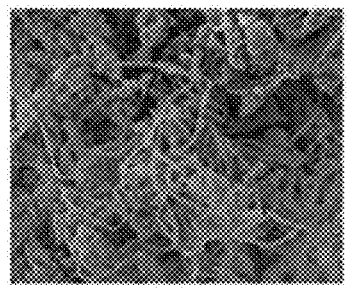
FIGS. 5A-5E. SEM images of *M. gypseum* micrograph after treatment with 1.25% essential oil and (G&H) ethanol extract image of *Indian Costus*, showing the change in spore founs and disruption of hyphae.
Figure 5B:
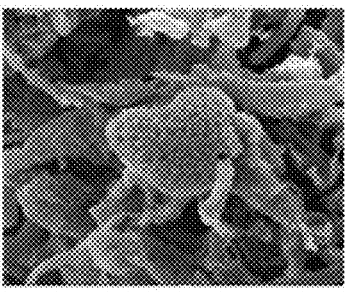
Figure 5C:
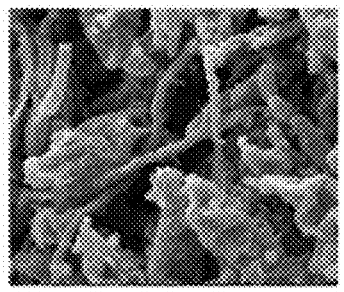
Figure 5D:
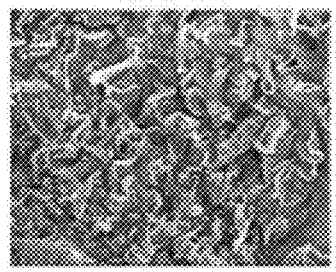
Figure 5E:
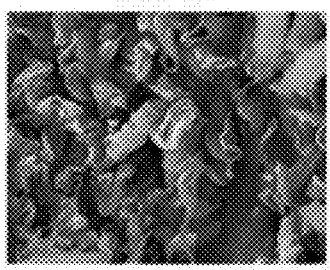

The SEM images obtained for the essential oil efficiency on *M. gypseum* hyphae and spores showed that treatment with the essential oil led to hyphae disruptions and changes in the general shape of the fungal spores (FIGS. 4 and 5).

The same extract concentrations of *Costus* on pathogenic bacteria showed that the growth of *P. aeruginosa* was more affected by *Costus* essential oil than by the ethanol and methanol extracts.

Figure 6:
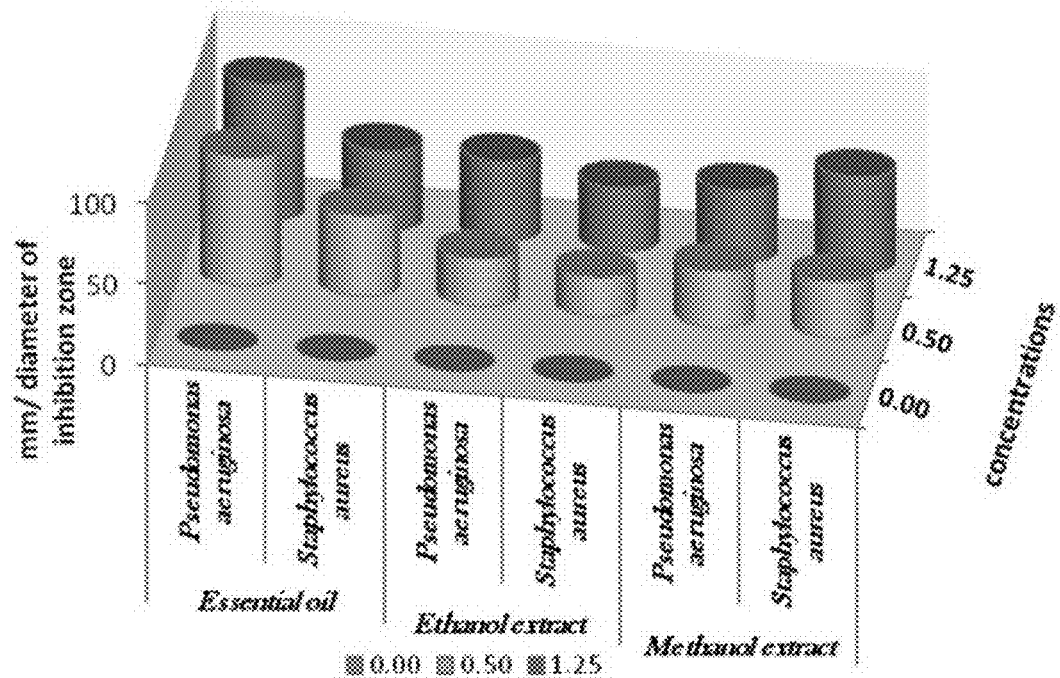
FIG. 6. Effect of various concentrations of *Indian Costus* extracts against *P. aeruginosa*, and *S. aureus* grown on blood media (mm/diameter of inhibition zone).

On the other hand, the inhibition zone measurements were 60 and 50 mm for methanol and essential oil on *S. aureus*, whereas the *Costus* methanolic extract was very effective on these bacteria (FIG. 6).

Indian *Costus* diosgenin was effective against *M. gypseum* at 1.25 m. However, it was not as effective against *C. tropicalis* and *C. albicans* growth when used in the same extract concentrations.

Figure 7:
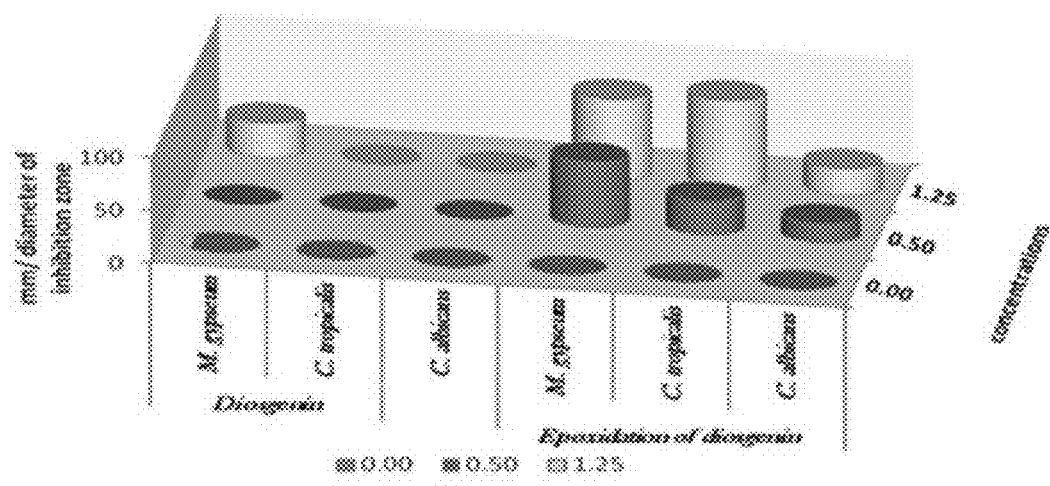
FIG. 7. Effect of various concentrations of diosgenin and diosgenin epoxide against *M. gypseum, C. tropicalis* and *C. albicans* grown on sabaroud dextrose media (mm/diameter of inhibition zone).
Figures 8A, 8B, 8C:
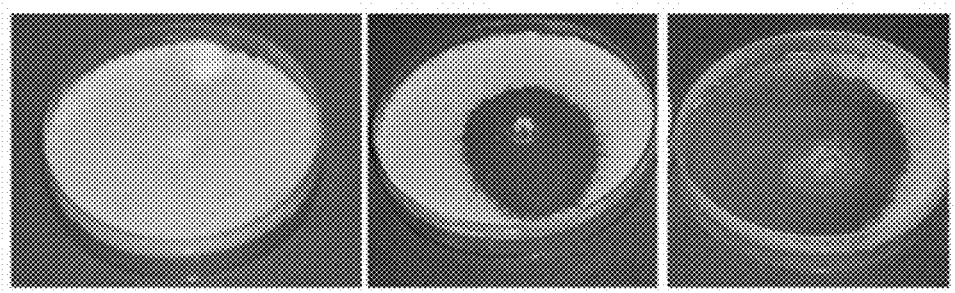
FIGS. 8A, 8B and 8C. Effect of diosgenin epoxide on *Microsporum gypseum* growth.

The epoxidation of diosgenin resulted in more activity than the diosgenin extract against the fungus and yeasts (FIGS. 7 and 8) where, the results for the inhibition zone measurements were 76, 82 and 25 mm compared with the sample.

Based on previous reports, the Indian *Costus* roots have several of medicinal components items that are used in the treatment of several diseases. *Saussurea Costus* is a popular medicinal plant, with sesquiterpene lactones as major phyto constituents and contains other pharmacological compounds such as costunolide, dehydro *Costus* lactone and cynampicrin which exhibit anti-inflammatory, anti-ulcer, anticancer and hepatoproteetive activities in vitro and in vivo models; Pandey M M, Rastogi S, Rawat A K. *Saussurea Costus botanical, chemical and pharmacological review of anayurvedic medicinal plant*. J Ethnopharmacol 2007; 110: 379-390.

Reports by have shown the antioxidant activity of the medicinal plant *Costus speciosus* which has been used for diabetic males by treatment of costunolide and eremanthin, those compounds are isolated from this plant by gas chromatography-mass spectrometry (GC-MS) analysis: Eliza J, Daisy P. Ignacimuthu S, Duraipandiyan V. *Antidiabetic and antilipidemic effect of eremanthin from Costus speciosus (Koen) Sm., in STZ-induced diabetic rats*. Chem Biol Interact 2009; 1: 67-72; Eliza J, Daisy P, Ignacimuthu S. *Antioxidant activity of costunolide and eremanthin isolated from Costus speciosus (Koen ex. Retz) Sm*. Chemm, Biol Interact 2010; 3: 467-472. However, the antibacterial and antifungal activities were very high with by dichloromethane and methanol extracts, which were isolated from species of Aipinia, Costus and Zingiber; Habsah M, Amran M, Mackeen M M, Lajis N H, Kikuzaki H, Nakatani N A, Rahman A, Ali A M. *Screening of Zingiberaceae extracts for antimicrobial and anti-oxidant activities*. J Ethnopharmacol 2000; 72: 403-410. The essential oil, methanol and ethanol extracts of *Costus* roots contain an antimicrobial activity, and methanolic and aqueous extracts of *Costus arabicus*, one of 12 Yemeni herbs that are used as traditional medicine for human cancer cells, have demonstrated an inhibitory effect against grain-positive, three gram-negative bacterial and one fungal stains as well as three resistant *Staphylococcus* strains; Mothana R A, Gruenert R, Bednarski P J, Lindequist U. *Evaluation of the in vitro anticancer, antimicrobial and antioxidant activities of some Yemeni plants used in folk medicine*. Pharmazie 2009; 4: 260-268.32. Al-Kattan M O. *Effect A-wazarin2 preparation from camel's urine on some pathogenic Bactria for digestive system*. PhD Thesis 2006; 60-68.

The results obtained from revealed the efficiency of the dried roots and aquatic extracts (hot and cold) of Indian *Costus* used in high concentrations against *Aspergillus niger, A. flavus, A. fumigatus* and *C. albicans*. Concentrations of 20%, 25% and 30% were highly effective against the tested fungus, yeast and bacteria, which are respiratory pathogens; Al-Kattan M O. *Effect A-wazarin2 preparation from camel's urine on some pathogenic Bactria for digestive system*. PhD Thesis 2006; 60-68; AL-Kattan M O, AL-Sheikh H M. *Effect of water extract of Indian Costus or sea-Qust on pathogenic fungi for the respiratory system in human to exhibit the miracle scientific in the Sunah*. Ass Univ Bull Environ Res 2011; 14: 1-14. As shown herein, the roots of Indian *Costus* species contain several chemical compounds that are curative for dermatophyte infections.

As shown herein, antimicrobial activities of particular Indian *Costus* extracts were tested on fungi, yeast and bacteria. Fine powder from the dried roots of Indian *Costus* was used to extract the essential oil. Epoxidation of the extract was performed with m-chloroperbenzoic acid with $CHCl_3$ in a nitrogen atmosphere. The extracts and essential oil were tested for their antimicrobial activity. After treatment with essential oil extract, the change in the general shape of the fungal spores was examined by SEM analysis. The results showed that treatment by the essential oil led to hyphae disruptions and changes in the general shape of the fungal spores. The studies on the antimicrobial activity showed high growth inhibition in *M. gypseum, M. canis, C. albicans, P. aeruginosa* and *S. aureus*. Moreover, treatment by oil extract showed greater inhibitory effects on the fungi and yeast than the methanol and ethanol extracts and epoxidation of diosgenin resulted in evermore activity than diosgenin extract against the fungus and yeasts.

The inventors have identified specific extracts, components, and derivatives of *Costus* components, namely epoxidated diosgenin, that exhibit useful therapeutic activities and may be used as alternatives or adjuncts to antibiotics.

The invention claimed is:

1. A method for inhibiting the growth of at least one microorganism comprising contacting the at least one microorganism with a *Costus speciosis* extract comprising epoxidized diosgenin, wherein said at lcast one microorganism is *Microsporum, Candida, Pseudomonas* or *Staphylococcus*.

2. The method of claim 1, wherein the extract of *Costus speciosis* is an essential oil extract.

3. The method of claim 1, wherein the extract of *Costus speciosis* is a methanol extract.

4. The method of claim 1, wherein the extract of *Costus speciosis* is an ethanol extract.

5. The method of claim 1, wherein the at least one microorganism is *Microsporum*.

6. The method of claim 1, wherein the at least one microorganism is *Candida*.

7. The method of claim 1, wherein the at least one microorganism is selected from the group consisting of *M. gypsum, M. tropicalis, M. canis* and *C. albicans*.

8. The method of claim 1, wherein the at least one microorganism is *Pseudomonas aeruginosa*.

9. The method of claim 1, wherein the at least one microorganism is *Pseudomonas* or *Staphylococcus aureus*.

10. The method of claim 1, wherein the at least one microorganism is in the skin, hair or nails of a subject having tinea.

11. The method of claim 1, wherein the at least one microorganism is associated with a sinus or respiratory infection.

12. The method of claim 1, wherein the at least one microorganism is associated with a burn, wound or skin or mucous membrane infection.

13. The method of claim 1, wherein the at least one microorganism is in a diabetic ulcer or wound.

14. The method of claim 1, wherein the *Costus speciosis* extract comprises *Costus* components soluble in methanol.

15. The method of claim 1, wherein the *Costus speciosis* extract comprises *Costus* components soluble in ethanol.

16. The method of claim 1, wherein the *Costus speciosis* extract comprises substantially pure epoxidized diosgenin.

17. The method of claim 1, wherein the contacting comprises topically administering a composition containing at least 1 wt % of *Costus* extract containing epoxidized disgenin to a subject in need thereof.

* * * * *